United States Patent [19]

Gil et al.

[11] Patent Number: 5,100,790
[45] Date of Patent: Mar. 31, 1992

[54] PROCESS FOR OBTAINING IRONE BY ENZYMATIC ROUTE

[75] Inventors: Gérard Gil, Aubagne; Jean Le Petit, Allauch; Jean-Louis Seris, Jurancon, all of France

[73] Assignee: Societe Nationale Elf Aquitaine, Paris, France

[21] Appl. No.: 658,742

[22] Filed: Feb. 21, 1991

[30] Foreign Application Priority Data

Feb. 22, 1990 [FR] France .................................. 90 02212

[51] Int. Cl.$^5$ ............................ C12N 5/00; C12P 7/26
[52] U.S. Cl. ...................................... 435/148; 435/192; 435/240.54
[58] Field of Search ..................... 435/148, 192, 240.54

[56] References Cited

U.S. PATENT DOCUMENTS 4,963,480  10/1990  Belcour et al. ..................... 435/148

FOREIGN PATENT DOCUMENTS 2620702  3/1989  France .

OTHER PUBLICATIONS

Derwent Abs 90-104334/14 Hasegawa J02055796 (2-1990).
Derwent Abs 72-00730T/01 Essential Oil Cultures SU-293843 (1972).
W. Krick et al., "Isolation and Structure Determination of the Precursors and α- and γ-Irone and Homologous Compounds from *Iris pallida* and *Iris florentina*", pp. 179-184 (1983).
Marner et al., "Irigermanal and Iridogermanal: Two New Triterpenoids from Rhizomes of *Iris germanica* L." J. Org. Chem. vol. 47, No. 13, 1982.

*Primary Examiner*—Herbert J. Lilling
*Attorney, Agent, or Firm*—Foley & Lardner

[57] ABSTRACT

The subject-matter of the present invention is a process for obtaining irone by enzymatic route.

The precursors extracted from fresh iris rhizomes are subjected to the action of a peroxidizing enzymatic composition comprising oxygen and a lipoxidase or hydrogen peroxide and a peroxidase.

11 Claims, No Drawings

PROCESS FOR OBTAINING IRONE BY ENZYMATIC ROUTE

The present invention relates to a process for obtaining irone, the mixtures of the three isomers of which, $\alpha$, $\beta$ and $\gamma$, are used in the food industry and in the cosmetic and perfume industries for their odour of violets.

When they are harvested, the rhizomes of the iris contain hardly any irone and it is during prolonged storage that the odorous molecules appear, according to Z. Naturforsch. 38c 179-184 (1983), probably as a result of oxidative degradation of terpenoids.

In the conventional process for the preparation of irone, this oxidation takes place very slowly in decorticated rhizomes stored in cool and aerated premises, and it is necessary to wait more than two years after the harvest before a reasonable amount of irone can be extracted from the rhizomes by means of an organic solvent or steam stripping.

Nevertheless, it has recently been shown in the patent application FR-A-2 620 702 that chemical oxidation of the precursors, in particular triterpene precursors, extracted from the rhizomes by a lipophilic solvent without waiting for them to mature, enables irone to be isolated under conditions which make it economically worthwhile. The yields of irone extracted per unit weight of dry rhizome are higher in this procedure, which, in addition, requires neither the decortication of the rhizomes, necessary if maturation in air is to occur to an adequate extent, nor their prolonged storage.

The process according to the invention also involves the oxidation of the precursors extracted from the rhizomes not long after harvesting, without the length of time elapsed being critical and possibly after drying them in air in order to remove part of the water and to facilitate the transport. This oxidation is no longer carried out by chemical means, as this precludes the use of the irone obtained in the food industry, but by enzymatic means in the presence of a peroxidizing composition. This process, the implementation of which is particularly simple, makes it possible to obtain irone in yields at least three times higher than those of the standard process.

According to the invention, the precursors of more or less dry fresh iris rhizomes are extracted by means of a solvent of lipophilic molecules, and the extraction residue is subjected to the action of a peroxidizing enzymatic composition comprising hydrogen peroxide and a peroxidase or oxygen and a lipoxidase, optionally in the presence of a substrate of the enzyme, for example dihydroxyfumaric acid or ascorbic acid in the case of peroxidase or an unsaturated aliphatic carboxylic acid capable of giving rise to a hydroperoxide in the presence of the lipoxidase, such as linoleic acid, linolenic acid or arachidonic acid.

The first step of extraction of the terpene precursors from the rhizomes is performed on crushed or even ground rhizomes, preferably with a lipophilic solvent usually used in the flavouring industry, such as an alcoholic solvent, methanol or ethanol, a chlorinated solvent, methylene chloride or dichloroethane, or an aromatic or aliphatic hydrocarbon, such as benzene or hexane, usually at the reflux temperature of the solvent; optionally it is possible to use mixtures of solvents or perform two successive extractions with different solvents. It is preferable to use alcoholic or chlorinated solvents, which are better solvents for terpene substances than the hydrocarbons, and best to use methanol and methylene chloride. In order to remove the water-soluble substances drawn off in the extract, it is also possible to redissolve the residue obtained after evaporation in a solvent immiscible with water, such as methylene chloride, and to wash the organic phase with water before removing the organic solvent again.

The second step of enzymatic oxidation is performed under usual conditions, in water, optionally in the presence of a surfactant such as a fatty acid ester of sorbitol (Tween) or a co-solvent which improves the dispersibility of the hydrophobic molecules in the aqueous medium without denaturating the enzymes, such as dioxane, tetrahydrofuran or an alcohol, at the temperature and pH most favourable to the activity of the enzyme, usually between 25° C. and 35° C. at an alkaline pH.

Lipoxidases are found in many vegetables: aubergine, tomato, potato or soya bean; the one usually used and which is commercially available is the soya bean lipoxidase. The peroxidases are also present in many vegetables, but the most common is horseradish peroxidase; mention may also be made of the manganese peroxidases and the chloroperoxidases, which can be isolated from various micro-organisms, or the lactoperoxidase of milk.

It is known that the irone obtained is capable of being degraded by oxidation and the reaction time should not be extended beyond the time required for its formation. The specialist will be able to determine the most favourable concentration of reagents in the medium and the reaction time by means of preliminary assays; the progress of the reaction may be monitored by means of gas chromatography.

The irone is isolated by steam stripping or by extraction with a solvent immiscible with water.

In the following, examples of the implementation of the invention are described.

EXAMPLE 1

1st step: Extraction of the Precursors 2.5 kg of rhizomes of the iris Pallida of Italy, dried but still containing 60% water, are cleaned and placed in a 60 l stainless steel vessel equipped with a rotating paddle stirrer and containing 24 l of 96% ethanol; the mixture is maintained at the reflux temperature of the solvent for 20 h, then cooled to room temperature and filtered; the filtrate is concentrated to dryness in a vacuum; the solids filtered off are reintroduced in the vessel in 12 ml of methylene chloride and the mixture is maintained at the reflux temperature of the solvent for 20 h, then filtered at room temperature, the filtrate is concentrated to dryness in a vacuum and the residue, combined with the previous one, is redissolved in 2 l of methylene chloride. The organic phase is washed twice with water and evaporated to dryness to give 1 kg of dry extract, which will be subjected to enzymatic peroxidation.

2nd Step: Production of Irone 10 g of extract are suspended in 90 ml of an aqueous solution buffered with sodium borate (0.01M, pH 9.2); 10 ml of dioxane and 0.17 g of 6 units per mg soya bean lipoxidase, marketed by Fluka, are added. The mixture is vigorously stirred in an oxygen atmosphere at 30° C. for 24 h; the reaction mixture is then steam stripped using about 1 l of water; the amount of irone separated is determined by gas chromatography. 0.77 g of irone is thus obtained per kg of dry weight of starting rhizome.

When the reaction is prolonged to 48 h, 1.8 g of irone are obtained per kg of dry weight of rhizome; the chemical oxidation gives approximately the same result.

EXAMPLE 2

The same procedure as in example 1 is used except that linoleic acid is introduced into the reaction medium during the second step at a concentration of $10^{-3}$M.

After 24 h, 1.8 g of irone are thus obtained, and if the reaction is prolonged to 48 h, 2.2 g of irone are obtained per kg of dry weight of starting rhizome.

EXAMPLE 3

10 g of extract dissolved in 20 ml of dioxane are introduced into 100 ml of phosphate buffer (pH 8, 10 mM) containing 40 mg of horseradish peroxidase and 0.3 $\mu$mole of hydrogen peroxide. The peroxidase has an enzymatic activity of 100 units/mg, one unit corresponding to 1 $\mu$mole of gaiacol converted per min. and per mg of enzyme. After 60 h, the irone formed is steam stripped. 680 mg of irone are thus isolated per kg of dry weight of rhizome; in the absence of enzyme, only 50 mg/kg of irone are formed.

EXAMPLE 4

The same procedure is used as in example 3 except that 4.38 mg of ascorbic acid are also introduced into the medium. 400 mg/kg of irone are then formed in 24 h and 450 mg/kg in 60 h.

We claim:

1. An enzymatic process for obtaining irone, which comprises the steps of:
   (a) treating a lipophilic extract of fresh iris rhizomes, obtained with a solvent selected from the group consisting of alcoholic solvents, chlorinated solvents, aliphatic hydrocarbons, aromatic hydrocarbons and mixtures thereof, in an aqueous reaction medium, with a composition having peroxidizing activity, said composition comprising either oxygen and a lipoxidase, or hydrogen peroxide and a peroxidase; whereby irone precursors in said extract are oxidized to irone; and
   (b) recovering resultant irone.

2. Process according to claim 1, wherein said composition having peroxidizing activity comprises a lipoxidase and oxygen.

3. Process according to claim 1, wherein the reaction medium further comprises an unsaturated aliphatic carboxylic acid capable of giving rise to a hydroperoxide in the presence of a lipoxidase.

4. Process according to claim 1, wherein the reaction medium further comprises linolenic acid or linoleic acid.

5. Process according to claim 1, wherein said composition having peroxidizing activity comprises hydrogen peroxide and a peroxidase.

6. Process according to claim 1, wherein the reaction medium further contains a surfactant.

7. Process according to claim 1, wherein the reaction medium further comprises a co-solvent.

8. Process according to claim 7, wherein said co-solvent is dioxane or tetrahydrofuran.

9. Process according to claim 1, wherein said solvent is selected from the group consisting of methanol, ethanol and methylene chloride.

10. A process according to claim 1, wherein said treating occurs in the presence of a substrate for the enzyme.

11. A process according to claim 1, wherein said lipophilic extract of iris rhizomes is obtained with a solvent selected from the group consisting of benzene, hexane and dichloroethane.

* * * * *